United States Patent

Suzuki et al.

[11] Patent Number: 5,931,159
[45] Date of Patent: Aug. 3, 1999

[54] LUNG VENTILATOR

[75] Inventors: Tetsuya Suzuki, Katsushika-ku; Katsuyuki Miyasaka, Setagaya-ku, both of Japan

[73] Assignee: Origin Medical Instrument Co., Ltd., Tokyo, Japan

[21] Appl. No.: 08/872,185

[22] Filed: Jun. 10, 1997

Related U.S. Application Data

[63] Continuation of application No. 08/536,256, Sep. 9, 1995, abandoned.

[51] Int. Cl.$^6$ .............................. A61M 16/00; A62B 7/00
[52] U.S. Cl. ................................ 128/204.18; 128/204.21; 128/204.23
[58] Field of Search ....................... 128/204.18, 204.21, 128/204.23, 205.11

[56] References Cited

U.S. PATENT DOCUMENTS

| | | | |
|---|---|---|---|
| 3,586,021 | 6/1971 | McGuinness | 128/204.24 |
| 4,022,234 | 5/1977 | Dobritz | 128/205.11 |
| 4,023,587 | 5/1977 | Dobritz | 128/205.11 |
| 4,340,044 | 7/1982 | Levy et al. | 128/204.21 |
| 5,072,728 | 12/1991 | Pasterneck | 128/204.18 |
| 5,237,987 | 8/1993 | Andersen et al. | 128/204.18 |
| 5,358,387 | 10/1994 | Suzuki et al. | 417/295 |
| 5,452,714 | 9/1995 | Andersen et al. | 128/205.11 |
| 5,520,172 | 5/1996 | Obermayer | 128/205.13 |

FOREIGN PATENT DOCUMENTS

| | | | |
|---|---|---|---|
| 26-13-084 | 10/1976 | France | 128/205.11 |
| 1304-821-A | 4/1987 | U.S.S.R. | 128/205.11 |

*Primary Examiner*—John G. Weiss
*Assistant Examiner*—Joseph F. Weiss, Jr.
*Attorney, Agent, or Firm*—Antonelli, Terry, Stout & Kraus, LLP

[57] ABSTRACT

A lung ventilator for supplying a mixture of oxygen and air to a patient as inspiration gas. The lung ventilator includes a compressor having an intake line for taking in oxygen and gas and supplying a mixture of the oxygen and gas to a main flow line as the inspiration gas to the patient. A recycle line is connected to the main flow line and the intake line of the compressor and a control arrangement is provided for enabling a flow of a portion of the inspiration gas in the main flow line in excess of the inspiration gas utilized by the patient into the recycle line for supply to the intake line of the compressor.

9 Claims, 6 Drawing Sheets

LUNG VENTILATOR

This application is a continuation application of Ser. No. 08/536,256, filed Sep. 9, 1995, now abandoned.

BACKGROUND OF THE INVENTION

The present invention relates to a lung ventilator used for maintaining or assisting respiration and particularly to a small-sized and lightweight lung ventilator which is able to be used for a moderate or slight respiration disorder patient and suitable for use in a sickroom, at home, or in an ambulance for other than a serious respiration disorder patient requiring care in an intensive care unit.

In this kind of simple lung ventilator, a piston type pump is conventionally used as a means for supplying inspiration gas to a patient.

FIG. 1 is an illustration showing the constitution of the conventional gas supply pump and FIG. 2 is a graph showing a change in the airway pressure of a patient during inspiration by denoting time (second) in the abscissa and airway pressure (Paw) of a patient in the ordinate.

In FIG. 1, numeral 30 indicates a flexible bellows made of rubber or other materials, 31 a Suction valve, 32 an outlet valve, 33 a piston, 34 a screw, 35 a motor, 36 a rotary encoder, and 37 a position sensor for controlling the expanded and contracted positions of the rubber bellows 30. Namely, the gas supply pump of the conventional lung ventilator is a piston type pump, in which the rotating motion of the motor 35 is changed to linear reciprocating motion of the piston 33 so as to suck or eject gas by expansion or contraction of the rubber bellows 30.

In this gas supply pump system, a pressure sensor (not shown in the drawing) detects a reduction in the pressure in the respiration circuit when a patient starts inspiration and sends an operation start signal to the motor 35. However, the time lag between the start of rotation of the motor 35 and actual arrival of inspiration gas at the patient is great, therefore the airway pressure of the patient is changed to negative pressure, as indicated by portion M as shown in FIG. 2 during this period. This is a load in respiration work for the patient, which is contrary to the original purpose of the lung ventilator, i.e., reducing the respiration workload.

As a solution for the above problem, a continuance flow type lung ventilator is known.

FIG. 3 is a flow diagram showing the constitution of the conventional continuance flow type lung ventilator.

In the lung ventilator shown in FIG. 3, air which is ejected from an air compressor 1A via an air pressure regulator 40, and oxygen which is supplied from a separated oxygen source (not shown in the drawing) via an oxygen pressure regulator 41, are blended by an oxygen blender 42 so as to adjust the oxygen density and provide for the continuance flow. The flow rate of the continuance flow is adjusted by a flow controller 43, and which is supplied to the patient.

In the case of spontaneous breathing, the patient breathes freely and gas expired by the patient is exhaled through an exhalation valve 10. A pressure meter 13 and an inspiration safety valve 14 are installed in the inspiration circuit so as to insure the safety of the lung of the patient in the inspiration pressure applied thereto.

Flow lines branching from the inspiration circuit are installed, to which are equipped with such as a three-way solenoid valve 11A, a PEEP (positive expiratory end pressure) valve 12A, and a PEEP adjustment valve 44 so as to open or close the exhalation valve 10.

In this continuance flow type lung ventilator, the exhalation valve 10 is usually opened so as to continuously supply the inspiration flow required by a patient, thereby the patient breathes freely. When it is necessary to forcibly apply pressure to the lungs of the patient, the exhalation valve 10 is closed during the period of that time.

In the conventional continuance flow type lung ventilator shown in FIG. 3, there is a problem that when it is necessary to increase oxygen density in the inspiration flow, for example, when the inspiration flow rate is 30 l/min and the oxygen density is 100%, an oxygen flow of the rate of 30 l/min is continuously necessary, and the consumption of oxygen is high. Therefore, any home oxygen concentrator for home use having an oxygen gas flow rate from 5 to 6 l/min is not sufficient to supply the necessary large quantity of oxygen.

Namely, in a continuance flow type lung ventilator of the prior art, the inspiration gas of air and oxygen to be supplied is made constant in pressure by the respective pressure regulators, and then the flow rate thereof is controlled, so that the performance required for the air compressor comes up to operational pressure of 2 to 3 kg/cm$^2$ and a maximum flow rate of 100 l/min. Therefore, the air compressor meeting these conditions requires a motor of 100 to 200 W. However, it is impossible for a battery to drive such motor because it is too large and heavy.

As shown in FIG. 3, the lung ventilator requires the air pressure regulator 40, the oxygen pressure regulator 41, the oxygen blender 42, and the flow controller 43, and there is a problem that it is contrary to the requirements for a lung ventilator, i.e., small-sized, lightweight, and simple operation.

SUMMARY OF THE INVENTION

The present invention is intended to solve the above problems of the prior art, and an object of the present invention is to provide a continuance flow type lung ventilator for eliminating the time lag of the initial inspiration flow so as to reduce the respiration workload of the patient, as well as reducing the oxygen consumption, and supplying oxygen to the patient by use of the home oxygen concentrator.

Another object of the present invention is to provide a small-sized and simplified lung ventilator which does not require the complicated device constitution such as the conventional one, and can be driven by three power sources such as a storage battery, a car power source, and a commercial power source.

To accomplish the above first object, a lung ventilator according to the present invention comprises an air compressor, a main flow line connected to the outlet of air compressor so as to supply the inspiration gas to the patient, a recycle line which branches from the main flow line and extends to the intake side of the air compressor, and a control means for ejecting excessive inspiration gas which is not sucked by the patient to the recycle line.

Furthermore, to accomplish the above first object, a lung ventilator according to the present invention comprises an air compressor, wherein a pressure relief valve for keeping the airway pressure of the patient constant and a bypass valve for returning excessive inspiration gas which is not consumed by the patient during spontaneous breathing to the air compressor are provided to a flow line which is connected to the outlet side of the air compressor so as to supply the inspiration gas to the patient, the flow lines are downstream from the pressure relief valve and the bypass valve are joined so as to form a recycle line, the recycle line is connected with a suction intake and outside air intake of the air compressor so as to constitute a flow line, and a variable capacity reservoir equipped with an oxygen mixer is connected to the outside air intake.

To accomplish the above second object, a lung ventilator according to the present invention is such that in addition to the aforementioned constitution of lung ventilator, the air compressor is of an oil-less scroll type air compressor, and a control circuit is structured so as to supply a continuance flow of the inspiration gas at a predetermined flow rate by changing the rotational speed of the motor. Since the flow rate control can be obtained with little pressure loss in this manner, the necessary output of the motor lowers to 40 to 50 W, so that the motor which can be driven by a battery can be adopted, and a convenient lung ventilator of a three-way power supply type system can be provided.

The operation by the aforementioned technical means in the lung ventilator according to the present invention is summarized as shown below.

The oxygen flow consumed by a patient comes generally up to 5 to 6 l/min at flow rate. Therefore, according to the present invention, the inspiration gas, which is conventionally ejected outside via an exhalation valve when a patient does not inspire, is collected and recycled by the suction of the air compressor via a recycle line which is newly installed, and the variable capacity reservoir is installed on the suction side of the air compressor, for storing the mixed gas of necessary density from the oxygen mixer, thereby supplying an equivalent amount of the inspiration gas inspired by the patient. By doing this, the oxygen consumption by the lung ventilator can be reduced.

Moreover, in the aforementioned new oxygen supply method, the inspiration gas flow rate to be supplied to a patient can be controlled by changing the rotational speed of the motor of the air compressor (scroll air compressor). Therefore, the air pressure regulator, oxygen pressure regulator, and flow controller of the prior art can be abolished, and the oxygen blender can be replaced with an extremely simplified one, thereby the lung ventilator as the whole apparatus can be simplified.

As mentioned above, according to the present invention, a continuance flow type lung ventilator can be provided, for which the time lag of the initial inspiration flow is eliminated so as to reduce the respiration workload of a patient, the oxygen consumption is reduced, and oxygen can be supplied by use of a home oxygen concentrator.

Furthermore, according to the present invention, a small-sized and simplified lung ventilator which does not require a complicated device constitution such as the conventional kind of apparatus and can be driven selectively by three power sources can be provided.

The foregoing and other objects and features of the present invention will be understood from the following detailed description of embodiments in connection with the accompanying drawings.

DESCRIPTION OF THE PREFERRED EMBODIMENTS

Firstly, the device constitution of the lung ventilator shown in FIG. 4 will be explained.

Figure 1:
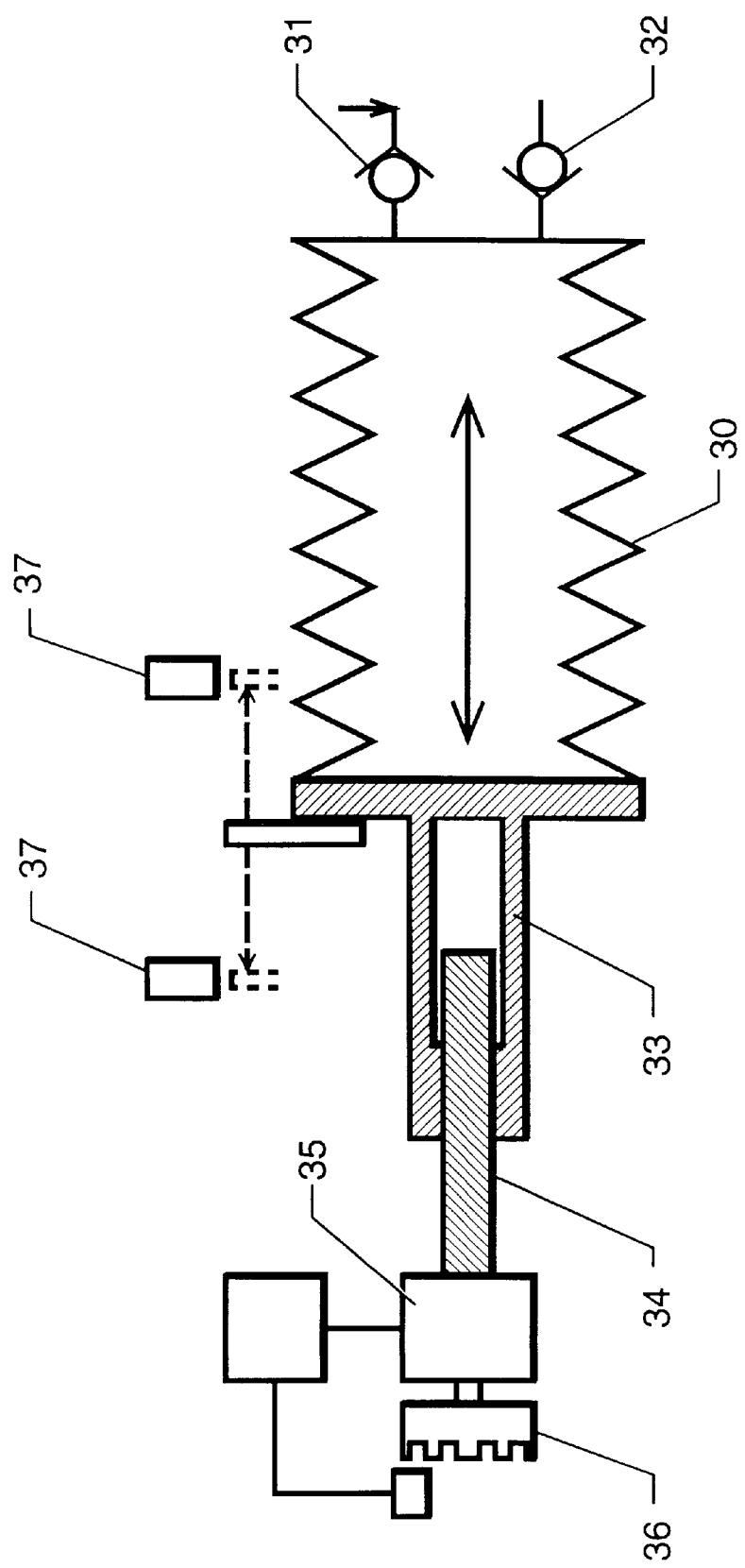
FIG. 1 is an illustrative drawing showing the constitution of a conventional gas supply pump of a lung ventilator.
Figure 2:
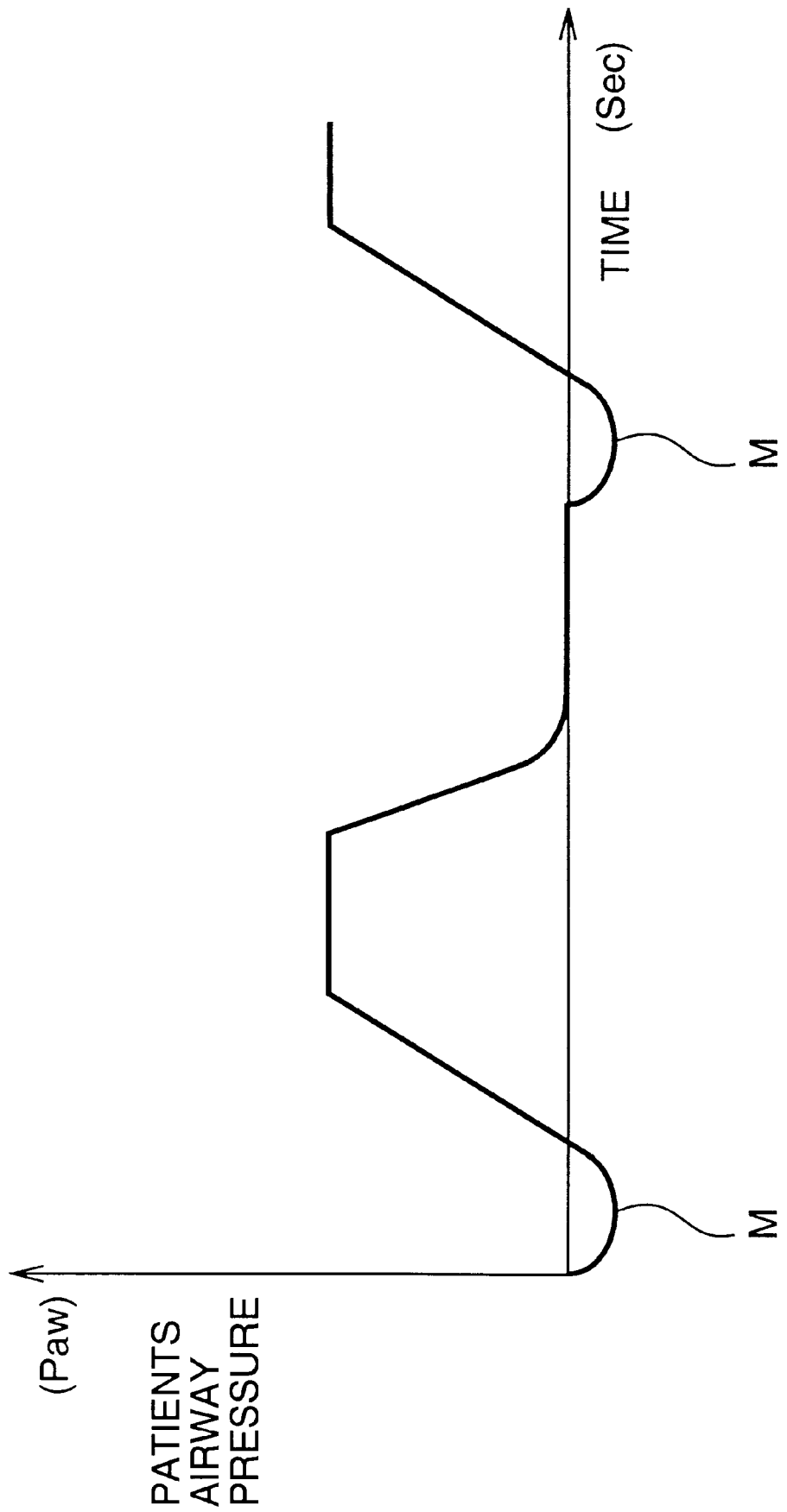
FIG. 2 is a graph showing a change in the airway pressure of a patient during inspiration when the apparatus shown in FIG. 1 is used.
Figure 3:
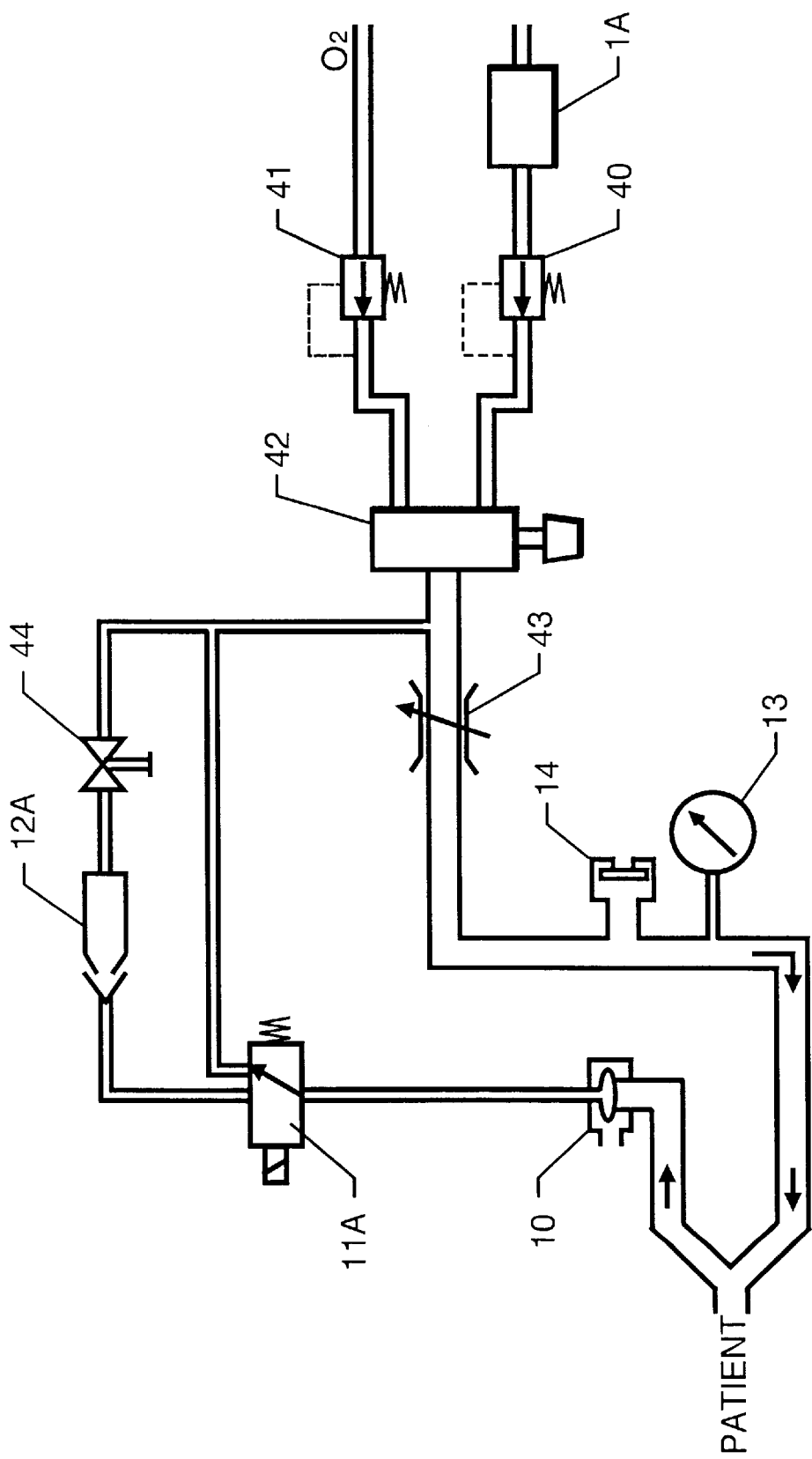
FIG. 3 is a flow diagram showing the constitution of a conventional continuance flow type lung ventilator.
Figure 4:
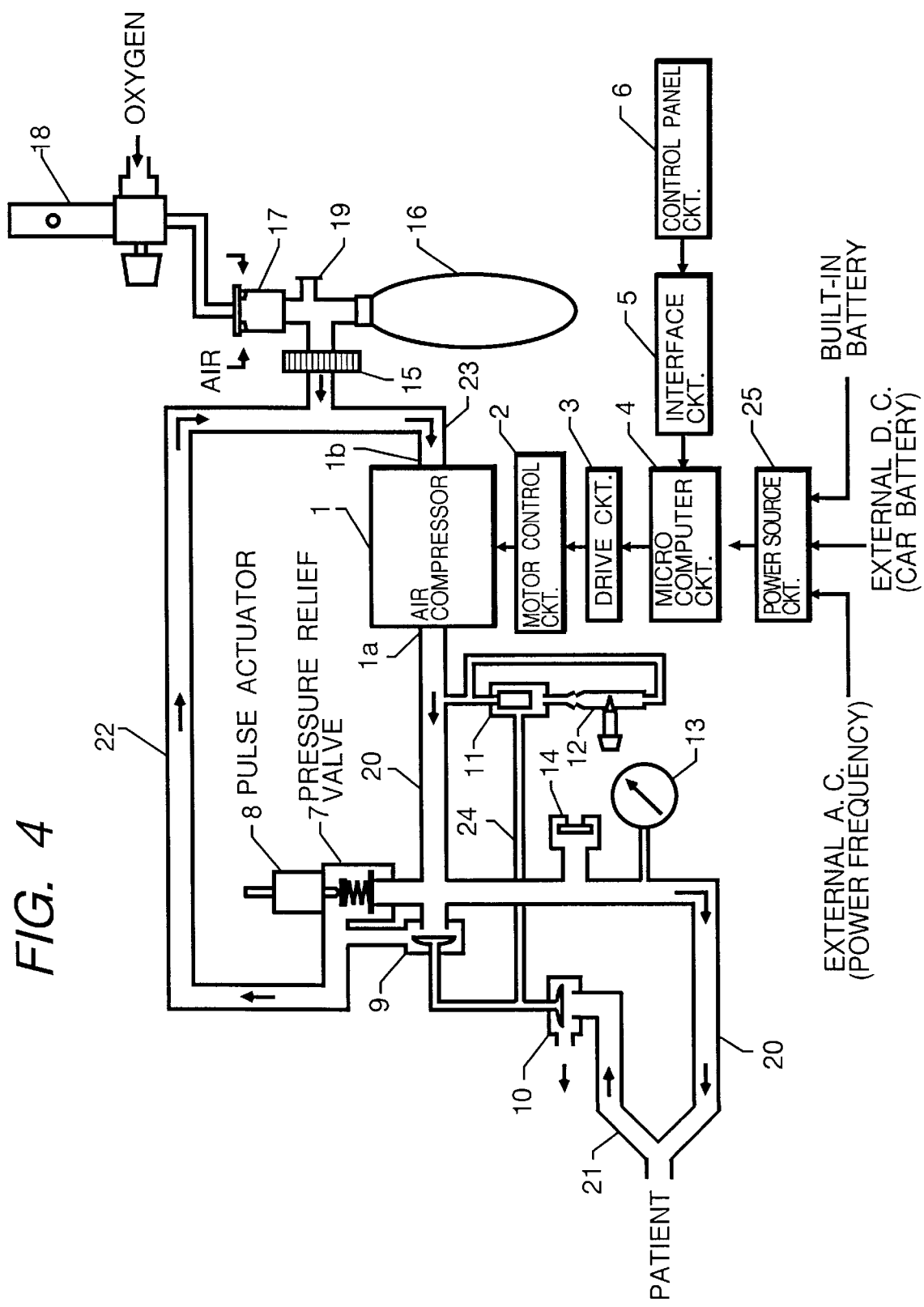
FIG. 4 is a flow diagram of a lung ventilator according to an embodiment of the present invention.
Figure 5:
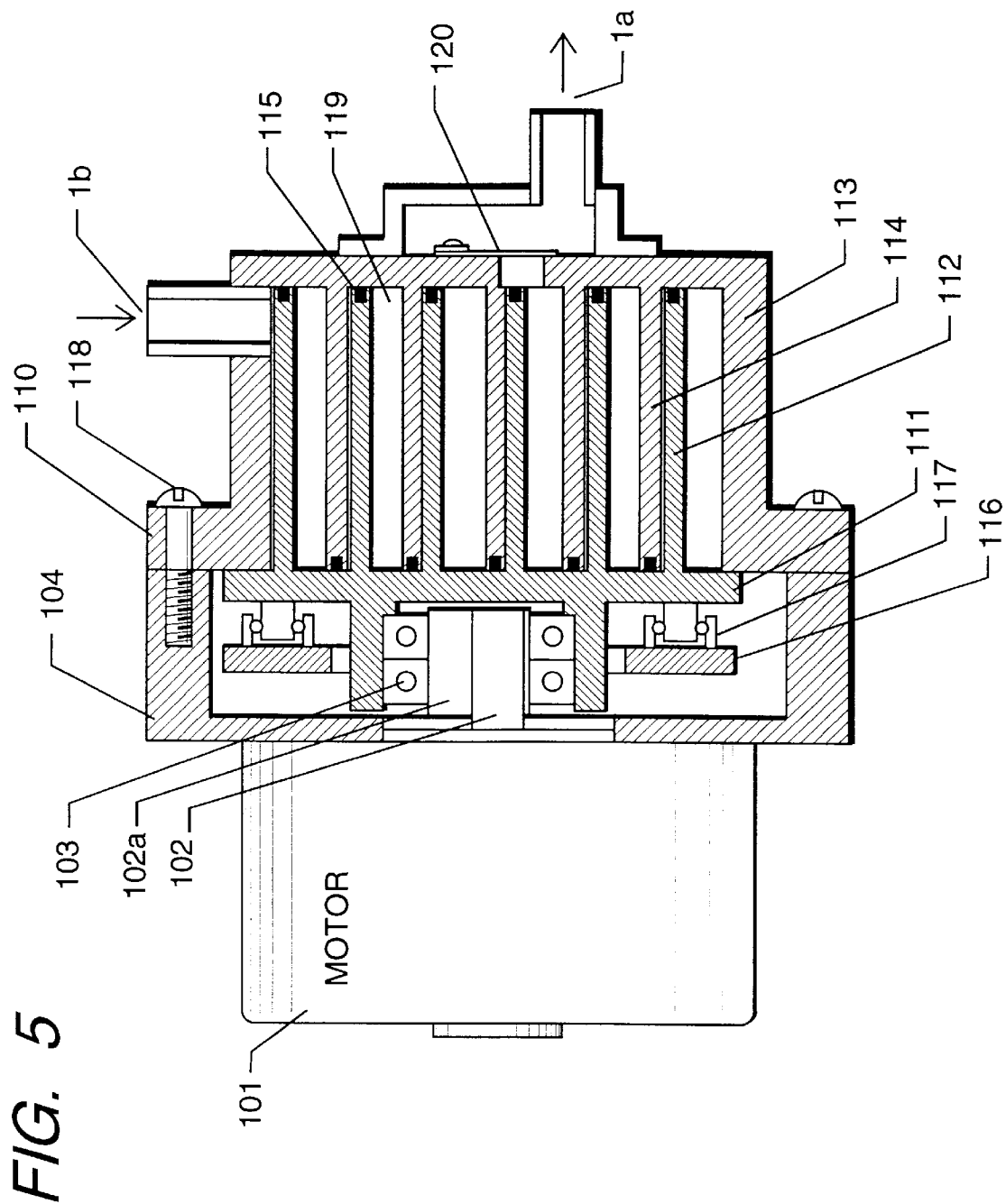
FIG. 5 is a longitudinal cross sectional view of a scroll air compressor which is applied to the present invention.

In FIG. 4, numeral 1 indicates an air compressor having a function for compressing and blowing a mixture of air and oxygen, and according to the present invention, preferably, an oil-less scroll air compressor which will be described later by FIG. 5 is applied thereto.

For the air compressor 1, a motor control circuit 2, a drive circuit 3, a micro computer circuit 4, an interface circuit 5, and a control panel circuit 6 are provided so as to constitute a control circuit thereof.

Numeral 7 indicates a pressure relief valve for keeping the airway pressure of a patient constant, 8 a pulse actuator for operating the pressure relief valve 7, 9 a bypass valve for returning excessive inspiration gas which is not consumed by the patient during spontaneous respiration back to the inlet of the air compressor 1, 10 an exhalation valve, 11 a three-way solenoid valve, 12 a PEEP valve, 13 a pressure meter, and 14 an inspiration safety valve.

Numeral 15 indicates an air intake installed at the suction side of the air compressor 1, 16 a variable capacity reservoir for storing mixed gas of a necessary density and for supplying an amount of gas equivalent to that inspired by the patient (hereinafter referred to as just a reservoir), 17 an oxygen mixer, and 18 an oxygen flow meter provided on a pipe line for conducting oxygen from an oxygen concentrator or oxygen source (not shown in the drawing) which is separately installed to the oxygen mixer 17.

Furthermore, in FIG. 4, numeral 20 indicates an inspiratory flow line extending from a delivery outlet 1a of the air compressor 1 to the airway of a patient, 21 an expiratory flow line extending from the airway of the patient to the exhalation valve 10, and 22 a recycle line (by pass line) to which the down-stream flow lines of the pressure relief valve 7 and the bypass valve 9 are connected. The recycle line 22 is connected at the other end thereof to a compressor suction line 23 together with the air intake 15. The compressor suction line 23 is connected to a suction inlet 1b of the air compressor 1, and 24 denotes an exhalation valve line for opening or closing the bypass valve 9 and the exhalation valve 10. The exhalation valve line 24 is connected through the three-way solenoid valve 11 to the inspiratory flow line 20 as well as to the PEEP valve 12 at one end, and is connected to the bypass valve 9 and the exhalation valve 10 at the other end.

A numeral 25 indicates a power source circuit for supplying power to each unit of the apparatus. The power source comprises three sources such as a built-in storage battery, an external DC power source such as a storage battery of a car, and an external AC power source such as a commercial power source. The power source circuit 25 selects the three-system types of power sources in accordance with the priority, then it converts if needed and supplies the power with a voltage necessary to each unit of the apparatus. It is desirable to set the above priority, for example, in an order of the external AC power source, external DC power source, and built-in battery.

Next, the outline of the scroll air compressor used in this embodiment will be explained with reference to FIG. 5. Recently, a scroll air compressor is widely used, such as to compress refrigerant gas in the freezing cycle of a freezer or an air conditioner. However, there is no case that a scroll air compressor is applied under the condition of low pressure and comparatively high flow rate, such as the airway pressure of about max. 0.1 kg/cm$^2$ and the flow rate of about 20 to 100 l/min.

In the present invention, as an inspiration gas supply means of a simpler continuance flow type lung ventilator, a small-sized, and lightweight and oil-less scroll type air compressor of about 40 W, such as shown in FIG. 5, and a control circuit thereof are used.

The scroll air compressor shown in FIG. 5 comprises a motor 101 and a pump mechanism (compressing mechanism) 110 which are integrated with each other and a housing 104 at the motor side and a fixed scroll 113 are connected to each other with screws 118.

In FIG. 5, numeral 111 indicates a revolution scroll, 112 a scroll lap standing upright on the surface of the end plate of the revolution scroll 111, 113 a fixed scroll, and 114 a scroll lap standing upright on the surface of the table top plate of the fixed scroll. These laps 112 and 114 comprise involute curves and are combined so that the lap portions are engaged with each other. Numeral 115 indicates a gas leakage prevention packing installed at the tip of each lap.

Numeral 102 indicates a rotary shaft for transferring the driving force of the motor 101, and 102a an eccentric part thereof (hereinafter, just referred to as an eccentric shaft). The boss portion of the revolution scroll 111 is attached to the eccentric shaft 102a via a ball bearing 103 so that it can rotate.

Numeral 116 indicates a hollow and circular slide plate, 117 a pair of X-axial linear slide bearings installed on the slide plate 116 on the side of the revolution scroll 111. These bearings constitute a means for controlling the rotation of the revolution scroll 111 on its axis when the eccentric shaft 102a rotates, for allowing the revolution scroll 111 to revolve on a circular orbit with an eccentric radius, and for allowing the revolution scroll 111 to rotate around the fixed scroll 113, together with y-axial linear slide bearings (a pair of bearings are installed on the slide plate 116 on the side of the motor 101) which are not shown in the drawing.

In the scroll air compressor having the aforementioned constitution, gas is suctioned into the pump from a suction inlet 1b formed in a part of the fixed scroll 113 by driving the motor 101, and is compressed sequentially within a compressible space 119 which is formed by the revolution scroll lap 112 and the fixed scroll lap 114 which are engaged with each other. Then the compressed gas is led to the outlet 1a made in the center of the top plate of the fixed scroll 113, and is sent to the inspiratory flow line 20 shown in FIG. 4.

Next, the operation of the lung ventilator shown in the above will be explained.

When after setting a necessary oxygen density with the oxygen mixer 17 and oxygen is supplied to the oxygen mixer 17 from the home oxygen concentrator which is separately installed, the oxygen mixer 17 takes in necessary air by the venturi effect, and hence the reservoir 16 bulges, thereby a mixture of oxygen and air is stored in the reservoir 16. When the reservoir 16 is full of the mixture gas, the excessive gas is ejected outside from the safety valve 19.

The inspiration flow rate and inspiration pressure necessary for a patient are set in the control panel circuit 6. The set inspiration flow rate necessary for a patient is inputted to the micro computer circuit 4 via the interface circuit 5, and an instruction voltage is transmitted to the motor control circuit 2 from the micro computer circuit 4 via the drive circuit 3. Then, the scroll air compressor 1 (hereinafter, referred to as just the air compressor) starts running at the rotational speed corresponding to the set flow rate and the gas which is compressed in the pump mechanism 110 as mentioned above is sent to the inspiratory flow line 20 as inspiration gas flow. In this case, a pulse signal corresponding to the rotational speed from a hall effect device (not shown in the drawing), which is mounted in the motor 101, is fed back to the motor control circuit 2 so as to keep the rotational speed at that corresponding to the set inspiration flow rate, thereby the continuance flow of inspiration gas is supplied to a patient.

During the spontaneous respiration, as shown in FIG. 4, the three-way solenoid valve 11 is off, and the bypass valve 9 and the exhalation valve 10 are open. Namely, balloons 9a and 10a installed in the valve bodies of the bypass valve 9 and the exhalation valve 10 are shrunk to be flat. The inspiration gas flow ejected from the outlet 1a of the air compressor 1 passes through the bypass valve 9 and inlet 1b of the air compressor 1, via the recycle line 22, connected to the down-stream flow lines of the bypass valve 9 and the pressure relief valve 7.

When a patient breaths in, the inspiration gas is supplied to the patient without resistance and excessive gas passes through the bypass valve 9 and is recycled to the air compressor 1. An equivalent amount of gas breathed in by the patient is supplied from the reservoir 16 via the outside air intake 15. During mandatory respiration, the three-way solenoid valve 11 is kept in ON-PHASE for the inspiration time which is set and determined by a cycle of breathing rate per minute. For example, assuming the breathing rate as 15 breathes per minute, the three-way solenoid valve 11 turns ON and OFF repeatedly at intervals of 4 seconds. Although it is generally said that the ratio of the inspiration time to the expiration time is 1 to 2, the ratio depends on a patient.

Figure 6:
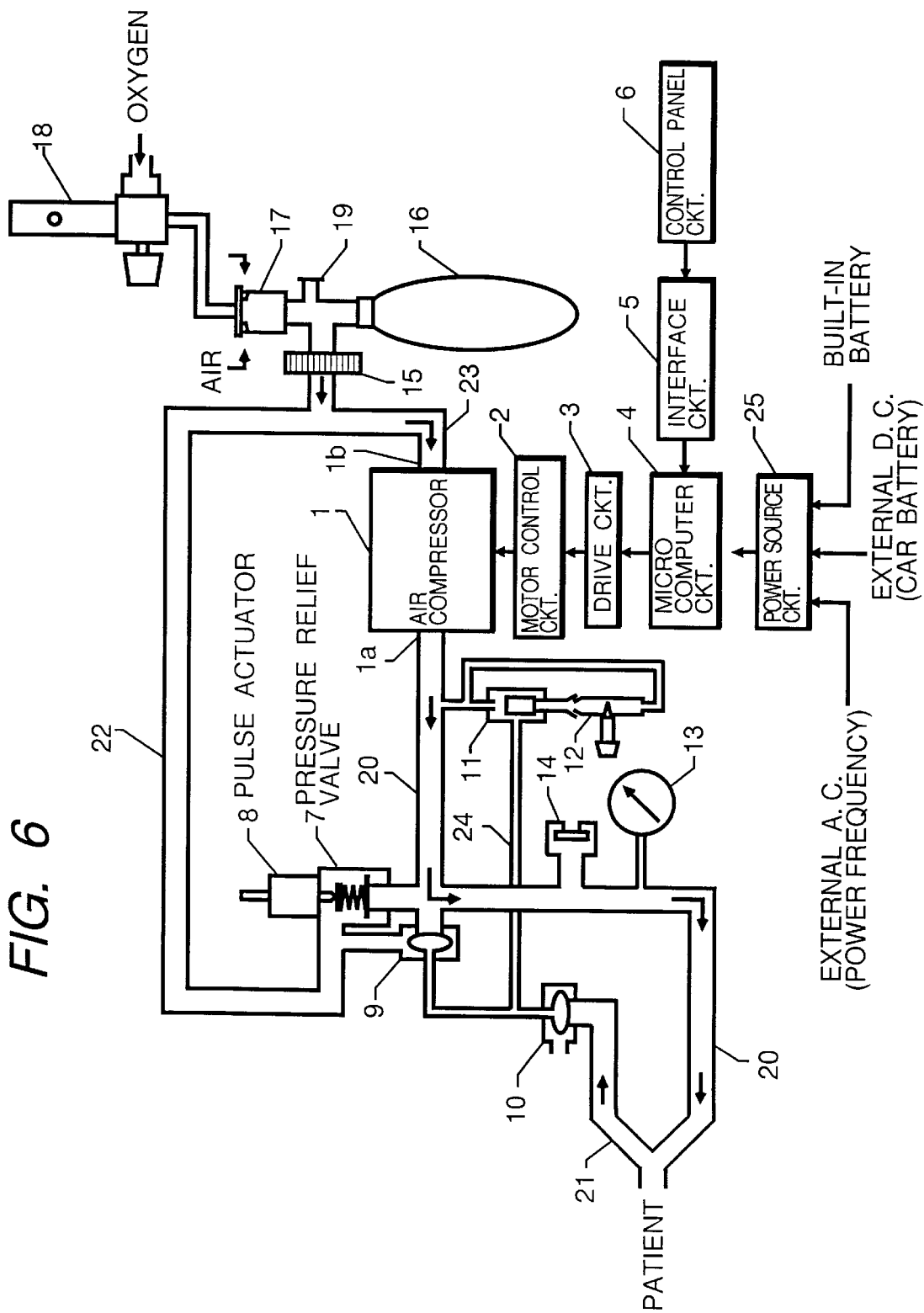
FIG. 6 is a flow diagram showing the flow of inspiration gas during mandatory respiration in the lung ventilator shown in FIG. 4.

The flow of inspiration gas during mandatory respiration is shown in FIG. 6.

The three-way solenoid valve 11 is turned ON in an inspiration time interval, a part of gas on the inspiratory flow line 20 reaches to the exhalation valve 10 and the bypass valve 9 via the exhalation valve line 24, and the balloons 10a and 9a installed in the two valve bodies bulge to close the exhalation valve 10 and the bypass valve 9. The pressure relief valve 7 is biased or pressed by a spring at the set inspiration pressure.

Gas to be inspired which is ejected from the air compressor 1 reaches a patient via the inspiratory flow line 20 and bulges and pressurizes the lungs of the patient. When the airway pressure increases and reaches the set pressure, the excessive gas is ejected from the pressure relief valve 7 to the down stream thereof, and is recycled to the suction inlet 1b of the air compressor 1 via the recycle line 22, thereby an equivalent amount of gas that was sent to the patient is supplied from the reservoir 16 via the outside air intake 15.

When the set inspiration time is over and the three-way solenoid valve 11 is turned off, the gas in the balloons 10a and 9a of the exhalation valve 10 and the bypass valve 9 is released from the PEEP valve 12, and the exhalation valve 10 and the bypass valve 9 are opened. Then, gas in the lungs of the patient is exhaled by the elasticity of the lungs outside from the exhalation valve 10. The gas ejected from the air compressor 1 passes through the bypass valve 9 as shown in FIG. 4 and is recycled to the suction inlet 1b of the air compressor 1 via the recycle line 22.

Hereinafter, the aforementioned inspiration and expiration are repeated in the set cycle.

Needless to say, however, the inspiratory flow line 20 is provided with the pressure meter 13 and the inspiration safety valve 14, so as to insure the safety in the inspiration pressure affecting the lung (airway) of a patient.

According to the above embodiment, a continuance flow type lung ventilator can be provided, for eliminating a time lag of the initial inspiration flow so as to reduce the respiration workload of a patient, reducing the oxygen consumption, and supplying oxygen by a home oxygen concentrator.

Furthermore, according to the above embodiment, a small-sized and simplified lung ventilator can be provided, which does not require complicated device parts, such as an air pressure regulator, an oxygen pressure regulator, an oxygen blender, and a flow controller in the conventional kind of apparatus, and can be alternatively driven by the three kinds of power sources, i.e., a storage battery, a car power source, or a domestic power source.

In the above, the operation of a pressure control type ventilation system, in which the airway pressure is limited by a set pressure, has been explained. However, the present invention is not limited to it and is also applicable to a volume control type ventilation system, in an operation of which the gas capacity entering into the lungs can be limited regardless of the pressure.

Although not shown in the drawing, the bypass valve 9, the pressure relief valve 7, and the PEEP valve 12 shown in the above embodiment can be unified or integrated as one pressure relief valve which can perform each operation according to the time schedule.

What is claimed is:

1. A lung ventilator for supplying a mixture of oxygen and air as inspiration gas to be consumed by a patient, comprising:

a compressor having an intake line for taking in oxygen and air and continuously supplying a mixture of the oxygen and air to a main flow line as the inspiration gas supplied at an outlet to the patient;

a recycle line connected to the main flow line at a position prior to the outlet of the main flow line and connected to the intake line of the compressor; and control means for enabling at least a flow of a portion of the continuously supplied inspiration gas in the main flow line in excess of consumption of the inspiration gas at the outlet by the patient into the recycle line for supply to the intake line of the compressor.

2. A lung ventilator according to claim 1, wherein the control means includes a pressure relief valve and a bypass valve coupled to the main flow line, the pressure relief valve being disposed for keeping an airway pressure of constant and the bypass valve being disposed for returning the excess inspiration gas which is not consumed during respiration to the recycle line, the pressure relief valve and the bypass valve having down-stream flow lines connected to the recycle line.

3. A lung ventilator according to claim 2, wherein the intake line for the compressor has an outside air intake, and a variable capacity reservoir having an oxygen mixer is connected to the outside air intake for the intake line of the compressor.

4. A lung ventilator according to claim 3, wherein the compressor is an air compressor, and the control means enables supply of a continuance flow at a predetermined inspiration gas flow of the inspiration gas rate by changing a rotational speed of a motor for driving the air compressor.

5. A lung ventilator according to claim 4, wherein the air compressor is a scroll air compressor.

6. A lung ventilator according to claim 2, wherein the compressor is an air compressor, and the control means enables supply of a continuance flow at a predetermined inspiration gas flow of the inspiration gas rate by changing a rotational speed of a motor for driving the air compressor.

7. A lung ventilator according to claim 6, wherein the air compressor is a scroll air compressor.

8. A lung ventilator according to claim 1, wherein the compressor is an air compressor, and the control means enables a continuance flow at a predetermined inspiration gas flow rate of the inspiration gas rate by changing a rotational speed of a motor for driving the air compressor.

9. A lung ventilator according to claim 8, wherein the air compressor is a scroll air compressor.

* * * * *